United States Patent [19]

Erhardt et al.

[11] Patent Number: 4,593,119
[45] Date of Patent: Jun. 3, 1986

[54] METHOD FOR TREATMENT OR PROPHYLAXIS OF CARDIAC DISORDERS

[75] Inventors: Paul W. Erhardt; Robert J. Borgman, both of Mundelein, Ill.; John P. O'Donnell, Morgantown, West Va.

[73] Assignee: American Hospital Supply Corporation, Evanston, Ill.

[21] Appl. No.: 450,228

[22] Filed: Dec. 16, 1982

Related U.S. Application Data

[62] Division of Ser. No. 211,345, Nov. 28, 1980, Pat. No. 4,387,103.

[51] Int. Cl.$^4$ .................. C07C 101/72; C07C 121/52
[52] U.S. Cl. ........................ 560/42; 560/22; 558/414
[58] Field of Search ............... 560/42, 45, 22; 260/465 D

[56] References Cited

U.S. PATENT DOCUMENTS

| | | | |
|---|---|---|---|
| 3,459,782 | 8/1969 | Koppe et al. | 560/42 |
| 3,644,469 | 2/1972 | Koppe et al. | 560/42 |
| 3,663,607 | 5/1972 | Barrett et al. | 560/42 |
| 3,740,444 | 6/1973 | Koppe et al. | 424/330 |
| 3,742,023 | 6/1973 | Koppe et al. | 560/42 |
| 3,836,671 | 9/1974 | Barrett et al. | 424/324 |
| 3,872,147 | 3/1975 | Koppe et al. | 560/42 |

FOREIGN PATENT DOCUMENTS

| | | |
|---|---|---|
| 0041491 | 12/1981 | European Pat. Off. |
| 0041492 | 12/1981 | European Pat. Off. |
| 2007751 | 2/1970 | Fed. Rep. of Germany |
| 153776 | 4/1971 | New Zealand |
| 2046259 | 11/1980 | United Kingdom |

OTHER PUBLICATIONS

Chem. Abstr., 80, 59728y (1974).
Chem. Abstr., 80, 95549z (1974).
Byrd et al, J. Am. Coll. Cardiology, vol. 3, No. 2, pp. 394–399 (Feb. 1984).

Primary Examiner—Natalie Trousof
Assistant Examiner—Bruce D. Gray
Attorney, Agent, or Firm—Bernard, Rothwell & Brown

[57] ABSTRACT

A method for the treatment or prophylaxis of cardiac disorders in a mammal, comprising administering to such mammal a short-acting β-blocking compound of the formula:

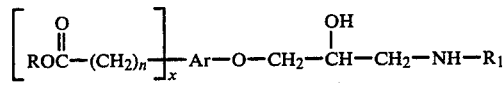

wherein R may be lower alkyl, aryl, or aralkyl; n may be an integer from 0 to about 10; x may be an integer from 1 to 3; Ar may be substituted or unsubstituted aromatic; R$_1$ may be lower alkyl, or aralkyl; and pharmaceutically accepted salts thereof. Novel compounds possessing short-acting β-adrenergic blocking activity are also disclosed.

6 Claims, No Drawings

METHOD FOR TREATMENT OR PROPHYLAXIS OF CARDIAC DISORDERS

This is a division of application Ser. No. 211,345 filed Nov. 28, 1980, U.S. Pat. No. 4,387,103.

BACKGROUND OF THE INVENTION

The present invention relates to the treatment or prophylaxis of cardiac disorders. More particularly, the invention relates to a novel method of treatment or prophylaxis of cardiac disorders which comprises administration of β-adrenergic blocking agents and to compounds useful in such method.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

β-Adrenergic stimulation may also aggravate or cause arrhythmias because of increased levels of catecholamines. Thus β-blocking agents may be employed to reduce the risks of arrhythmias.

Compounds have been discovered which selectively block β-adrenergic receptors in various organs. Beta receptors in the heart are generally referred to as $\beta_1$ receptors, and those associated with vasodilation and bronchodilation are $\beta_2$ receptors. Selective β-blockers are preferred for the treatment of cardiac disorders, because they may have less potential to cause hypertension or bronchoconstriction. A number of $\beta_1$ selective adrenergic blocking agents have been discovered. Smith, L. H., *J. Appl. Chem. Biotechnol.*, 28, 201–212 (1978). Most of such compounds are structural variations of 1-amino-3-aryloxy-2-propanol.

Heretofore, the emphasis in β-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional β-blocking agents can be employed for such treatment, but their duration of action may be much longer than desired by the physician. A β-blocking agent possessing a long duration of action does not allow precise control of heart work or prompt reversal of the β-blocking effect, which may be required in a critical care setting. For instance, if heart output becomes dangerously low, it is desirable to quickly reduce or eliminate β-blocking activity. The lingering activity of available β-blocking agents can be counterproductive and can greatly complicate the therapeutic decisions required of the physician during such critical care of cardiac patients.

Accordingly, there is a need for a pharmaceutical preparation and method of treatment, employing a β-adrenergic blocking agent having a short duration of action.

SUMMARY OF THE INVENTION

In accordance with the present invention, disclosed herein is a method for the treatment of prophylaxis of cardiac disorders in a mammal comprising administering to such mammal a short acting compound of the formula:

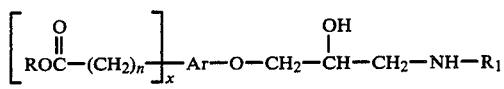

wherein R is lower alkyl, lower cycloalkyl, lower alkenyl, lower alkyl or aryl carboxymethyl, lower haloalkyl, aralkyl or aryl; n is an integer from 0 to about 10; x is an integer from 1 to 3, provided that when x is greater than 1, different occurances of the

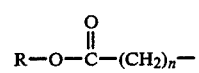

group may be the same or different; Ar is unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl or cyano; $R_1$ is lower alkyl, or aralkyl; or a pharmaceutically acceptable salt thereof.

DETAILED DESCRIPTION OF THE INVENTION

Compounds administered by the method of the present invention are represented by the formula:

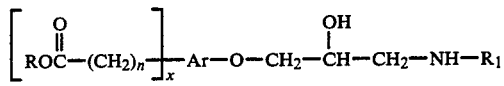

wherein R represents lower alkyl of straight or branched carbon chains from 1 to about 10 carbon atoms, lower cycloalkyl of from 1 to about 5 carbon atoms, lower alkenyl of from 2 to about 5 carbon atoms, lower alkynyl of from 2 to about 5 carbon atoms, lower alkyl carboxymethyl in which the alkyl portion contains from 1 to about 5 carbon atoms, aryl carboxymethyl in which the aryl portion contains from 6 to about 8 carbon atoms, lower haloalkyl of from 1 to about 5 carbon atoms, aryl of from 6 to about 10 carbon atoms or aralkyl wherein the alkyl portion contains from about 1 to about 5 carbon atoms and the aryl portion represents substituted or unsubstituted monocyclic or polycyclic aromatic or heterocyclic ring systems of from 6 to about 10 carbon atoms; n represents an integer from 0 to about 10; x represents an integer from 1 to 3, provided that when x is greater than 1, different occurences of the

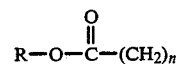

group may be the same or different; Ar represents substituted or unsubstituted aromatic, including monocyclic, polycyclic and heterocyclic ring systems, wherein aromatic substituents include lower alkyl of from 1 to about 10 carbon atoms, lower alkenyl or from 2 to about 10 carbon atoms, lower alkynyl of from 2 to about 10 carbon atoms, lower alkoxy of from 1 to about 10 carbon atoms, halogen, acetamido, amino, nitro, lower alkylamino, of from 1 to about 10 carbon atoms, hydroxy, lower hydroxy alkyl of from 1 to about 10 carbon atoms, and cyano; $R_1$ represents lower alkyl of from 1 to about 10 carbon atoms, such as methyl, propyl, hexyl, isopropyl, and the like; or aralkyl wherein the alkyl portion contains from 1 to about 5 carbon atoms and the aryl portion contains from 6 to about 10 carbon atoms, such as benzyl, phenethyl, naphthylethyl, 3,4-dimethoxyphenethyl and the like. Such compounds may be administered as their pharmaceutically acceptable acid addition salts, e.g., as the hydrochloride, sulfate, phosphate, gluconate, tartrate, etc.

In preferred compounds, n is an integer from 0 to about 5, and x is 1 or 2, and in particularly preferred compounds, Ar is phenyl, x is 1 or 2 and n is an integer from 0 to about 3. It has been found that the compounds in which Ar is phenyl and para-substituted, β-blocking potency and shortness of duration of action are improved when n is at least 1, i.e. the ester group is isolated from the aromatic ring by at least one methylene unit. Alternatively, in compounds in which Ar is phenyl, at least one of the ester-containing groups,

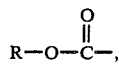

is advantageously in the ortho-position with respect to the side chain. It is surprising and presently unexplained, that two configurations of the compounds of the present invention, para-substitution with an ester carbonyl isolated from the aromatic ring and ortho-substitution with the ester carbonyl attached directly to the aromatic ring, provide enhanced β-blocking potency and relatively short duration of action.

In preferred compounds, the ester substituent, R, is lower alkyl of from 1 to about 5 carbon atoms, such as methyl, ethyl, n-butyl, n-pentyl, and the like; lower alkenyl of from 2 to about 5 carbon atoms, such as ethyl, 2-propenyl, 2-methyl-3-butenyl and the like, or lower cycloalkyl of from 3 to about 5 carbon atoms such as cyclopropyl, cyclopentyl, 2-methylcyclopropyl, and the like; $R_1$ is lower alkyl of from 1 to about 5 carbon atoms such as methyl, ethyl, propyl, t-butyl, pentyl and the like, or aralkyl, wherein the alkyl portion contains from 1 to about 5 carbon atoms and the aryl portion contains from 6 to about 10 carbon atoms, such as benzyl, phenethyl, dimethoxyphenethyl, naphthylethyl, phenylbutyl, and the like.

Aromatic substituents include lower alkyl of from 1 to about 5 carbon atoms, lower alkenyl of from 2 to about 5 carbon atoms, lower alkoxy of from 1 to about 5 carbon atoms, halogen, acetamido, amino, nitro, lower alkylamino of from 1 to about 5 carbon atoms, hydroxy, lower hydroxyalkyl of from 1 to about 5 carbon atoms, and cyano. Preferred aromatic substituents are lower alkyl of from 1 to about 5 carbon atoms, fluoro, chloro, and alkyl.

The compounds described herein may be prepared by any suitable procedure. The compounds are advantageously prepared by reacting an appropriate phenol derivative with epichlorohydrin in the presence of a base to form a 1,2-epoxy-3-aryloxypropane derivative according to the following reaction:

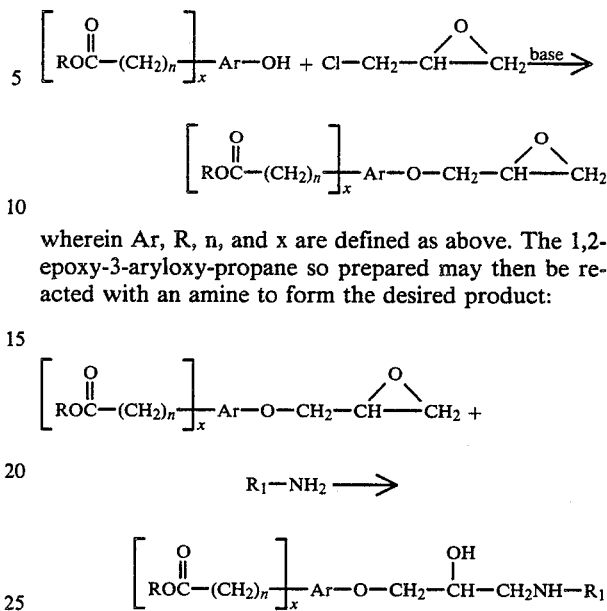

wherein Ar, R, n, and x are defined as above. The 1,2-epoxy-3-aryloxy-propane so prepared may then be reacted with an amine to form the desired product:

This reaction is preferably conducted in an alcoholic solvent identical to the ester adduct to prevent alcoholysis side reactions, e.g. when R is methyl, the reaction solvent is preferably methanol.

The phenol derivatives used as starting materials in the reaction scheme described above are generally commercially available compounds or may be prepared by methods known in the art. For instance, for the preparation of some preferred compounds of the present invention, suitable starting materials include methyl 2-hydroxybenzoate, methyl(4-hydroxyphenyl)acetate, methyl 4-hydroxyphenyl propionate, and the like.

The compounds of this invention are advantageously administered parenterally, e.g., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g. less than about three hours, the duration of effect is thought to be determined by both metabolic effects and distribution phenomena. For relatively long periods of infusion, e.g. greater than about three hours, the duration of effect is thought to depend largely on metabolic effects. Accordingly, although the present methods and compounds are generally useful for short term infusion therapy, certain compounds are preferred for longer durations of infusion. This principle is demonstrated by refererence to the 40 minute and three hour infusion studies described in Examples XXXVI-LI. The compounds have been found to be generally non-toxic within conventional dosage ranges. Dosages of about 0.001 to about 100 mg. per kg. of body weight per hour are generally employed, with preferred dosages ranging from about 0.01 to about 10 mg. per kg. of body weight per hour.

The present invention is further illustrated by the following examples which are not intended to be limiting.

EXAMPLE I

This example describes the experimental procedure for producing the following compound:

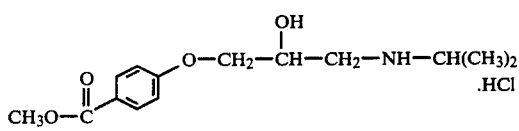

Methyl 4-(2,3-Epoxypropoxy)benzoate

A mixture of 15.2 gm (0.1 mole) of methyl 4-hydroxybenzoate, 27.6 gm (0.2 mole) potassium carbonate and 31 mL (0.4 mole) epichlorohydrin in 250 mL acetone was heated to reflux for 24 hours. The reaction medium was then filtered and evaporated. The residue was taken up in 100 mL toluene and washed with 100 mL 1.0N NaOH and 2×100 mL water. The toluene phase was then dried over magnesium sulfate and evaporated to provide the crude product as an oil. Purification was effected by vacuum distillation (66°-67°; 75 u pressure) and provided 14 gm (67%) of a clear oil when gradually crystallized at room temperature: mp 54°-55° C. The NMR and IR spectra and elemental analysis data were consistent with the assigned structure.

Methyl 4-[2-Hydroxy 3-(isopropylamino)propoxy]benzoate Hydrochloride

A mixture of 2.1 gm (0.01 mole) of the epoxide derivative described above and 0.9 mL (0.01 mole) of isopropylamine in 25 mL of methanol was heated to reflux for 2 hours. The reaction medium was evaporated to a clear oil which was then taken up in methanol and treated with ethereal HCl. Crystals formed at room temperature and provided 1.25 gm (41%) of product having a melting point of 168°-169° C. The NMR spectrum was consistent with the assigned structure and the elemental analysis was consistent with the molecular formula $C_{14}H_{22}ClNO_4$.

EXAMPLE II

This example describes the experimental procedure for producing the following compound:

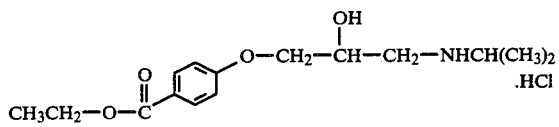

Ethyl 4-(2,3-Epoxypropoxy)benzoate

A mixture of 16.7 gm (0.10 mole) of ethyl 4-hydroxybenzoate, 20.7 gm (0.15 mole) of potassium carbonate and 24 mL (0.30 mole) of epichlorohydrin in 250 mL acetone was heated to reflux for 12 hours. The reaction medium was then filtered and evaporated. The resulting oil was taken up in 100 mL toluene and washed with 100 mL 1.0N sodium hydroxide and 2×100 mL water. The toluene phase was then dried over magnesium sulfate and evaporated to give 13.5 gm (61%) of a clear oil. The NMR spectrum of this oil was consistent with the assigned structure and the oil was used in the next reaction step without further purification.

Ethyl 4-[2-Hydroxy-3-(isopropylamino)propoxy]benzoate Hydrochloride

A mixture of 2.2 gm (0.01 mole) of the epoxide derivative prepared as described above and 25 mL (0.28 mole) of isopropylamine in 25 mL of ethanol was heated to reflux for 2 hours. The reaction medium was then evaporated to a clear oil which was dissolved in ethanol and treated with ethereal HCl. The white crystals which were produced (1.07 gm, 35%) had a melting point of 112°-114° C. The NMR spectrum was consistent with the assigned structure and the elemental analysis was consistent with the molecular formula $C_{15}H_{24}ClNO_4$.

EXAMPLE III

This example describes the experimental procedure for producing the following compound:

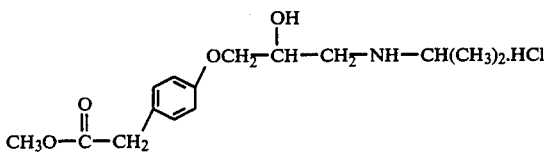

Methyl(4-Hydroxyphenyl)acetate

A solution of 15 gm (0.1 mole) of 4-hyroxyphenylacetic acid in 500 mL methanol and 2 mL concentrated sulfuric acid was placed in a Soxhlet extractor charged with 3A molecular sieves. The solution was heated to reflux for 72 hours, and the sieves were exchanged at 24-hour intervals. The reaction medium was then evaporated to an oil which was dissolved in 100 mL toluene and extracted with 3×100 mL water. The toluene phase was dried over magnesium sulfate, treated with activated charcoal and evaporated to provide 13 gm (80% yield) of a yellow oil. The NMR spectrum was consistent with the assigned structure and this material was used in the next reaction step.

Methyl 4-(2,3-Epoxypropoxy)phenylacetate

The oil described in the preceding reaction was utilized directly in the condensation reaction with epichlorohydrin, potassium carbonate and acetone as described in Example I to provide the desired aryl ether epoxide in 60% yield. The NMR spectrum of the clear oil obtained in this manner was consistent with the assigned structure.

Methyl 4-[2-Hydroxy-3-(isopropylamino)propoxy]phenylacetate hydrochloride

A mixture of 2.2 gm (0.01 mole) of methyl 4-(2,3-Epoxypropoxy)-phenylacetate and 1.7 mL (0.02 mole) of isopropylamine in 25 mL methanol was heated to reflux for 2.5 hours. The reaction medium was then evaporated, and the resulting oil was dissolved in methanol and treated with ethereal HCl to provide 0.6 g (19%) of white crystals: mp 119°-121°. The NMR spectrum was consistent with the assigned structure and the elemental analysis was consistent with the molecular formula $C_{15}H_{24}NO_4Cl$.

EXAMPLE IV

This example describes the experimental procedure for producing the following compound:

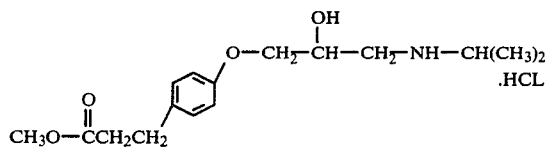

Methyl 3-(4-Hydroxyphenyl)propionate

A solution of 17 gm (0.1 mole) of 3-(4-hydroxyphenyl)propionic acid in 500 mL methanol and 2 mL concentrated sulfuric acid was placed in a Soxhlet extractor charged with 3A molecular sieves. The solution was refluxed for 72 hours and the sieve were exchanged at 24 hour intervals. The reaction medium was then evaporated to an oil which was dissolved in 100 mL toluene and extracted with 3×100 mL water. The toluene phase was dried over magnesium sulfate, treated with activated charcoal and evaporated to provide 15 gm (80%) of a clear oil. The NMR spectrum was consistent with the assigned structure and this material was utilized directly in the next reaction step.

Methyl 3-[4-(2,3-Epoxypropoxy)phenyl]propionate

The oil described above was utilized directly in the condensation reaction with the epichlorohydrin, potassium carbonate, and acetone as described in Example I. Purification was effected by vacuum distillation (156°; 0.4 mm pressure) and provided the aryl ether epoxide in 45% yield. The NMR spectrum of the clear oil obtained by this procedure was consistent with the assigned structure and the elemental analysis was consistent with the molecular formula $C_{13}H_{16}O_4Cl$.

Methyl 3-[4-[2-Hydroxy-3-(isopropylamino)propoxy]-phenyl]-propionate Hydrochloride A mixture of 50 gm (0.21 mole) of methyl 3-[4-(2,3-epoxypropoxy)phenyl]propionate and 100 mL of isopropylamine in 100 mL methanol was heated to reflux for 4 hours. The reaction medium was then evaporated and the resulting oil taken up in methanol and treated with ethereal HCl and provided crystals which were recrystallized in similar fashion to provide 28 gm (47%) of white crystals: mp 85°-86°. The NMR and IR spectra and the elemental analysis data were consistent with the assigned structure having a molecular formula of $C_{16}H_{26}NO_4Cl$.

EXAMPLES V-VII

These examples describe procedures for preparing the compounds identified in Table I. The procedure of Example IV was repeated in all essential details, except the amine reactant listed in Table I was substituted for isopropylamine. The NMR and IR spectra and elemental analyses of each of the compounds so prepared conformed to the assigned structure.

TABLE I

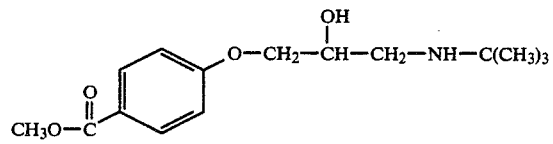

| Example | Amine Reactant $R_1$—$NH_2$ | $R_1$ | Melting Point |
|---|---|---|---|
| V | t-butylamine | t-butyl | 144–146° C. |
| VI | 3,4-dimethoxyphenethylamine | 3,4-dimethoxyphenethyl | 138–140° C. |
| VII | benzylamine | benzyl | 180–181° C. |

EXAMPLE VIII

This example describes experimental procedures for preparing the following compound:

Methyl 4-[2-Hydroxy-3-(t-butylamino)propoxy]benzoate

A mixture of methyl 4-(2,3-epoxypropoxy)benzoate (prepared as described in Example I) (2.1 g, 0.01 mole), 10 mL of t-butylamine and 10 mL of methanol was heated to reflux for three hours. The reaction medium was then evaporated under reduced pressure to provide the amine as an oil. The free amine was crystallized from hexane-ethyl acetate in 65% yield: m.p. 88°–89° C. The NMR spectrum and elemental analysis were consistent with the assigned structure.

EXAMPLES IX, X AND XI

These examples describe the preparation of the following compounds:

EXAMPLE IX

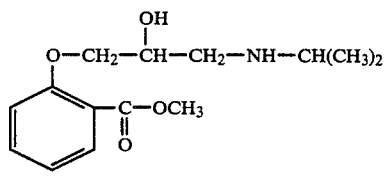

EXAMPLE X

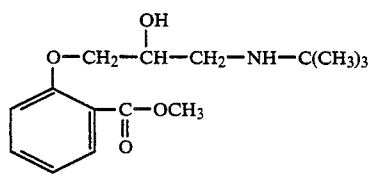

EXAMPLE XI

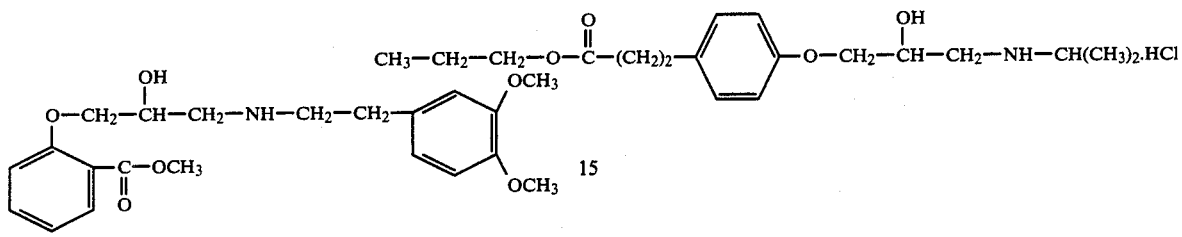

Methyl 2-(2,3-Epoxypropoxy)benzoate

A mixture of 15.2 g (0.10 mole) of methyl 2-hydroxybenzoate, 27.6 g (0.20 mole) of $K_2CO_3$ and 31 mL (0.40 mole) of epichlorohydrin in 250 mL of acetone was heated to reflux for 24 hours. The reaction medium was then filtered and evaporated under reduced pressure. The resulting oil was dissolved in 100 mL toluene and washed consecutively with 100 mL water, 2×100 mL 1.0N NaOH, and 2×100 mL water. The organic phase was then dried over $MgSO_4$ and evaporated under reduced pressure to provide the crude product as an oil. Purification was effected by vacuum distillation to provide an oil in 12% yield: boiling point 148° C. (75 u). The NMR and IR spectra and elemental analysis were consistent with the assigned structure.

Methyl 2-[2-Hydroxy-3-(isopropylamino)propoxy]benzoate (Example IX)

A mixture of 2.1 g (0.01 mole) of methyl 2-(2,3-epoxypropoxy)benzoate, 10 mL of isopropylamine and 10 mL of methanol was heated to reflux for three hours. The reaction medium was then evaporated under reduced pressure to provide the amine as an oil. The oil was treated with hexane:ethyl acetate (9:1) to generate the free amine as a crystalline product in 63% yield: m.p. 78°–79° C. The NMR spectrum and elemental analysis were consistent with the assigned structure.

Methyl 2-[2-Hydroxy-3-(t-butylamino)propoxy]benzoate Hydrochloride Hemihydrate (Example X)

This material was prepared by the same reaction used for the compound of Example IX except that t-butylamine was substituted for isopropylamine and the crystalline hydrochloride salt was prepared in 30% yield by adding aqueous HCl to a methanolic solution followed by trituration with ether: m.p. 116°–118° C. The NMR spectrum and elemental analysis were consistent with the assigned structure.

Methyl 2-[2-Hydroxy-3-(3,4-dimethoxyphenethylamino)-propoxy]benzoate Oxalate (Example XI)

This material was prepared by the same reaction used for the compound of Example IX except that 3,4-dimethoxyphenethylamine was substituted for isopropylamine, and the product was crystallized as its oxalate salt from methanol-ether in 25% yield: m.p. 125°–126° C. The NMR spectrum and elemental analysis were consistent with the assigned structure.

EXAMPLE XII

This example describes procedures for producing a compound of the formula n-Propyl 3-(4-Hydroxyphenyl)propionate

A solution of 15 g (0.09 mole) of 3-(4-hydroxyphenyl)propionic acid in 250 mL of n-propanol containing 5 drops of conc. $H_2SO_4$ was heated to reflux for 72 hr in a Soxhlet Extractor charged with 50 g of 3A molecular sieves. The reaction medium was then evaporated under reduced pressure and the resulting oil dissolved in 100 mL toluene and washed with three 50 mL portions of water. The toluene phase was then dried with $MgSO_4$ and evaporated under reduced pressure to provide 12 g (64%) of a clear oil which was utilized directly in the next step without additional purification. The NMR spectrum was consistent with the assigned structure.

n-Propyl 3-[4-(2,3-Epoxypropoxy)phenyl]propionate

A mixture of 9 g (0.04 mole) of n-propyl 3-(4-hydroxyphenyl)propionate, 10 g (0.08 mole) of $K_2CO_3$ and 12 mL (0.15 mole) of epichlorohydrin in 150 mL of acetone was stirred and heated to reflux for 20 hours. The reaction medium was then filtered and evaporated under reduced pressure. The resulting oil was taken up in 100 mL toluene and washed consecutively with 50 mL water 2×50 mL of 1N NaOH and 2×50 mL of water. The toluene phase was then dried over $MgSO_4$ and evaporated under reduced pressure to provide 3 g (30%) of a clear oil which was used directly in the next step without additional purification. The IR and NMR spectra of the reaction product were consistent with the assigned structure.

n-Propyl 3-[4-[2-Hydroxy-3-(isopropylamino)propoxy]phenyl]-propionate Hydrochloride A solution of 1.5 g (0.006 mole) of n-propyl 3-[4-(2,3-epoxypropoxy)phenyl]propionate in 10 mL of isopropylamine and 20 mL of n-propanol was heated to reflux for 4 hours. The reaction medium was then evaporated under reduced pressure to provide the crude free amine as an oil. The oil was dissolved in n-propanol and treated with ethereal HCl and provided 1.2 g (56%) of white crystals: mp 88°–92° C. The NMR spectrum of the product was consistent with the assigned structure and the elemental analysis data was consistent with the molecular formula $C_{18}H_{30}NO_4Cl$.

EXAMPLE XIII

The experiment of Example IV was repeated in all essential details to produce a compound of the formula

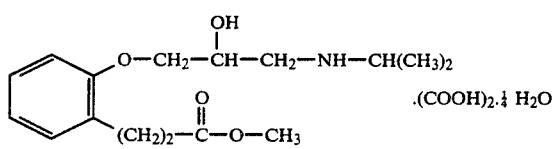

except that 3-(2-hydroxyphenyl)propionic acid was substituted for 3-(4-hydroxyphenyl)propionic acid, and the final product was crystallized as its oxalate salt from methanol-ether. The product melted at 92°–94° C. and NMR spectrum and elemental analysis were consistent with the assigned structure.

EXAMPLE XIV

This example describes procedures for producing a compound of the formula

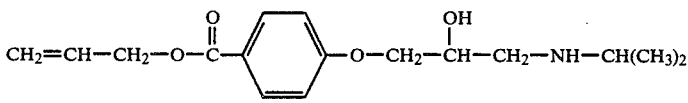

3-Propenyl 4-Hydroxybenzoate

A mixture of 27.6 g (0.2 mole) of 4-hydroxybenzoic acid, 13.8 g (0.1 mole) of $K_2CO_3$ and 24 g (0.2 mole) of allyl bromide in 350 mL of acetone; $H_2O$ (9:1) was heated to reflux for 3 hours. The acetone layer was separated and evaporated to dryness in vacuo and the residue was recrystallized from $CCl_4$ to give 19.7 g (55%) of white crystals: mp 92°–96°, whose NMR spectrum was consistent with the assigned structure.

3-Propenyl 4-(2,3-Epoxypropoxy)benzoate

The experimental procedure of Example I for preparing Methyl 4-(2,3-epoxypropoxy)benzoate was repeated in all essential details, except 3-propenyl 4-hydroxybenzoate was substituted for methyl 4-hydroxybenzoate. The reaction yielded a clear oil in 61% yield, whose NMR spectrum conformed with the assigned structure.

3-Propenyl 4-[2-Hydroxy-3-(isopropylamino)propoxy]benzoate

The experimental procedure of Example I for preparing methyl 4-[2-hydroxy-3-(isopropylamino)propoxy]benzoate hydrochloride was repeated in all essential details, except 3-propenyl 4-2,3(epoxypropoxy)benzoate was substituted for methyl 4-(2,3-epoxypropoxy)benzoate. Allyl alcohol was employed as the reaction solvent, and the reaction product was crystallized as the free amine from hexane:ethyl acetate (4:1) in approximately 25% yield. The product melted at 63°–64° C. and its NMR spectrum and elemental analysis conformed to the assigned structure.

EXAMPLES XV AND XVI

The procedures of Example XIV were repeated in all essential details to produce the compounds identified in Table II, except that 3-hydroxybenzoic acid was substituted for 4-hydroxybenzoic acid as the starting material in Example XV and 2-hydroxybenzoic acid was substituted for 4-hydroxybenzoic acid as the starting material in Example XVI. Both compounds were crystallized as their oxalate salts. The NMR spectra and elemental analyses of the compounds were consistent with the assigned structures.

TABLE II

| Example | Compound | Melting Point |
|---|---|---|
| XV | ![structure] O—CH$_2$—CH(OH)—CH$_2$—NH—CH(CH$_3$)$_2$ with C(=O)—O—CH$_2$—CH=CH$_2$ at meta position ·(COOH)$_2$ | 125–126° C. |
| XVI | ![structure] O—CH$_2$—CH(OH)—CH$_2$—NH—CH(CH$_3$)$_2$ with C(=O)—O—CH$_2$—CH=CH$_2$ at ortho position ·(COOH)$_2$ | 139–140° C. |

EXAMPLES XVII–XXXII

Several of the compounds of the present invention were tested for β-blocking activity in vitro using guinea pig right atria and guinea pig tracheal strips mounted in a tissue bath containing oxygenated (95% $O_2$–5% $CO_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 g. Changes in rate of response to isoproterenol, a standard β-receptor agonist, were measured in the absence and presence of test compounds. Spiral strips of guinea pig trachea were suspended under 5 g resting tension and incubated with phentolamine, tropolone, and cocaine. Active tension was generated by addition of carbachol ($3.0 \times 10^{-7}$M) and decreases in tension in response to isoproterenol were quantitated. Cumulative concentration response curves were produced with isoproterenol both before and after 60-minute incubation of test compounds with atria and trachea. Compounds with β-blocking activitiy shifted concentration response curves to the right. The blocking potency of test compounds was estimated by computing $pA_2$ values ($-\log K_B$) by the method of Furchgott (The Pharmacological Differentiation of Adrenergic Receptors., Ann. N.Y. Acad. Sci. 139:553–570, 1967). Comparison of blockade of right atrial and tracheal response to isoproterenol permits assessment of cardioselectivity of test compounds; i.e., cardioselective compounds are relatively more effective in blocking atrial rate than tracheal force responses to isoproterenol. The degree of cardioselectivity was estimated from the ratio $K_B$ trachea/$K_B$ atria 10($pA_2$ Atria $-pA^2$Trachea). A ratio greater than one indicates cardioselectivity.

The results obtained with several of the test compounds are contained in Table III. All of the compounds are β-blockers.

TABLE III

| Example | Test Compound (Numerical Designation Indicates Previous Example Which Describes Preparation of Compound) | pA$_2$ Atria | pA$_2$ Trachea | Cardio-selectivity |
|---------|---|---|---|---|
| XVII | IV | 7.0 | 5.6 | 30 |
| XVIII | V | 6.5 | 5.9 | 4 |
| XIX | VI | 6.5 | 5.2 | 20 |
| XX | VII | 5.9 | 4.9 | 10 |
| XXI | XII | 5.4 | 5.2 | 1.6 |
| XXII | XIII | 8.6 | 8.9 | 0.5 |
| XXIII | III | 6.4 | 5.4 | 10 |
| XXIV | XIV | 6.3 | 5.7 | 4 |
| XXV | XV | 6.9 | 7.2 | 2 |
| XXVI | XVI | 7.9 | 7.9 | 1 |
| XXVII | IX | 8.2 | 7.9 | 2 |
| XXVIII | I | 6.8 | 5.5 | 19 |
| XXIX | II | 6.5 | 6.1 | 2.5 |
| XXX | X | 8.8 | 8.9 | ~1 |
| XXXI | VIII | 6.5 | 5.4 | 32 |
| XXXII | XI | 8.3 | 7.1 | 16 |
| Propranolol | | 8.7 | 8.9 | ~0.7 |
| Practolol | | 6.6 | 5.8 | 6 |

EXAMPLE XXXIII

The duration of beta-blockage was determined in vivo using pentobarbital-anesthetized dogs instrumented for measurement of heart rate using a Beckman cardiotachometer triggered electronically by a phasic aortic blood pressure signal. Both vagus nerves were severed in the cervical region and the animals were mechanically ventilated. Two experimental designs were used. The first employed a 40-minute infusion of test compound and the second used a 3-hour infusion of test compound. In the 40-minute model, isoproterenol was infused into a foreleg vein at the rate of 0.5 mg/kg/min to induce a beta-receptor mediated tachcardia. Various doses of test compound were then infused into a femoral vein over a period of 40 minutes. This infusion was then terminated and recovery from blockade was quantitated. The percent inhibition of the heart rate response to isoproterenol after 40 minutes of infusion of the test compound was computed along with the total cumulative doses received over the 40-minute period. This cumulative dose is expressed as mg/kg and is an indication of potency. The time period required for 80% recovery of heart rate for each dose of test drug was also measured to quantitate duration of action. The potency and duration of action were normalized to a level of 50% inhibition of the isoproterenol response via least squares regression of data from each animal. Test compound were dissolved in 0.9% NaCl and infused at a rate of 0.05 ml/Mg/min or less. In the 3-hour infusion model, bolus doses of isoproterenol (0.5 mg/kg) were used to assess the degree of beta-blockade and recovery from beta-blockage after termination of the infusion. The doses were spaced at 10-minute intervals and were given before, during and following the infusion of test compounds. The infusion rate was adjusted so that the end of the 3-hour infusion period the degree of isoproterenol inhibition averaged about 50% of control. The results of the 40-minute infusion are shown in Table IV, and the results of the 3-hour infusion are shown in Table V.

TABLE IV

| Example | Test Compound (Numerical Designation Indicates Previous Example Which Describes Preparation of Compound) | Potency mg/kg/40 min | 80% Recovery Time | Number of Experiments |
|---|---|---|---|---|
| XXXIII | I | 3.7 ± 1.3 | 34 ± 11 | 3 |
| XXXIV | II | 5.7 ± 1.6 | 56 ± 6 | 3 |
| XXXV | X | 0.14 ± .04 | 12 ± 1 | 3 |
| XXXVI | III | 2.3 ± 0.6 | 20 ± 5 | 4 |
| XXXVII | IV | 1.35 ± 0.52 | 12 ± 2 | 4 |
| XXXVIII | V | 4.5 ± 1.5 | 7 ± 2 | 3 |
| XXXIX | IX | 0.176 ± 0.02 | 15 ± 2 | 4 |
| Propranolol | | 0.06 ± .01 | 42 ± 9 | 10 |
| Practolol | | | 61 | |

TABLE V

| Example | Test Compound (Numerical Designation Indicates Previous Example Which Describes Preparation of Compound) | Potency mg/kg/180 min | 80% Recovery Time | Number of Experiments |
|---|---|---|---|---|
| XL | XIII | 0.45 | 29 ± 6 | 4 |
| XLI | VI | 31.0 ± 7.0 | 14 ± 3 | 5 |
| XLII | IV | 9.0 | 12 ± 3 | 13 |
| XLIII | IX | 1.1 | 15 ± 2 | 5 |
| XLIV | XI | 2.5 ± 0.4 | 30 ± 4 | 3 |
| XLV | XVI | 3.5 ± 0.7 | 36 ± 5 | 5 |
| XLVI | XV | 12.8 | >60 | 4 |
| XLVII | X | 0.90 | 22 ± 5 | 6 |
| XLVIII | V | 30.4 | 15 ± 3 | 9 |
| Propranolol | | 0.225 | >60 | 6 |
| Practolol | | | >60 | |

EXAMPLE XLIX–LVII

These examples describe experiments which demonstrate the disappearance of the compounds of the present invention in vitro in human whole blood, dog whole blood, and dog liver homogenate. The rate of disappearance of a compound is expressed as the half-life ($T_{\frac{1}{2}}$), which is the time period in which one-half of the initial amount of compound tested disappears. In each experiment, 1 mL of a solution containing 50 µg of the test compound was added to 1 mL of whole blood or 1 mL of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 mL) was immediately added, and the mixtures were mixed to stop enzymatic hydrolysis. Zero time samples were prepared by adding 2 mL of acetonitrile to denature the proteins prior to addition of the test compounds. After centrifugation to sediment denatured proteins, 2 mL of the supernatant was removed and analyzed by high pressure liquid chromatography, using a mobile phase of 60% acetonitrile/40% 0.05M sodium phosphate buffer (pH 6.6), a U.V. detector, and a Waters u Bondapak Phenyl column. The half-life of each test compound was determined graphically by plotting the decrease in concentration as a function of time. The results of the experiments are shown in Table VI.

TABLE VI

| Example | Test Compound | $T_{\frac{1}{2}}$ (minutes) Human Blood | Dog Blood | Dog Liver |
| --- | --- | --- | --- | --- |
| XLIX | VI | 44 | 13 | 2 |
| L | X | 7 | 17 | 5 |
| LI | XI | 8 | 120 | 3 |
| LII | XIII | 11 | 120 | <2.5 |
| LIII | I | >60 | 60 | >180 |
| LIV | II | >60 | 60 | — |
| LV | IX | 7 | 38 | 19 |
| LVI | III | 2 | 60 | 5 |
| LVII | IV | 44 | 41 | <5 |

We claim:

1. A compound of the formula

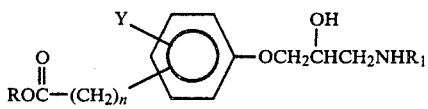

wherein R is methyl or ethyl; the ester-containing group is in the para position on the phenyl ring with respect to the amine-containing group; n is 2; $R_1$ is lower alkyl of from 1 to about 5 carbon atoms; and Y is hydrogen, lower alkyl of from 1 to about 5 carbon atoms, lower alkenyl of from 2 to about 5 carbon atoms, lower alkynyl of from 2 to about 5 carbon atoms, lower alkoxy of from 1 to about 5 carbon atoms, halogen, acetamido, amino, nitro, lower alkylamino of from 1 to about 5 carbon atoms, hydroxy, lower hydroxyalkyl of from 1 to about 5 carbon atoms, or cyano; or a pharmaceutically acceptable salt thereof.

2. The compound of claim 1, wherein Y is lower alkyl of form 1 to about 5 carbon atoms, fluoro or chlor.

3. The compound of claim 1, or 2, wherein R is methyl or ethyl, and $R_1$ is isopropyl or t-butyl.

4. The compund of claim 3, wherein $R_1$ is isopropyl.

5. The compound of claim 1, of the formula

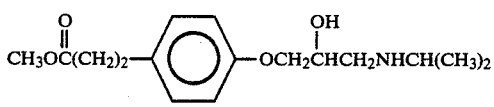

or its pharmaceutically acceptable salt.

6. The compound of claim 1, of the formula

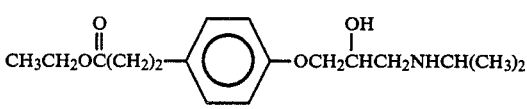

or its pharmaceutically acceptable salt.

* * * * *

UNITED STATES PATENT AND TRADEMARK OFFICE
CERTIFICATE OF CORRECTION

PATENT NO. : 4,593,119
DATED : June 3, 1986
INVENTOR(S) : Paul W. Erhardt et al.

It is certified that error appears in the above-identified patent and that said Letters Patent is hereby corrected as shown below:

Change the title to read: -- COMPOUNDS FOR TREATMENT OR PROPHYLAXIS OF CARDIAC DISORDERS --.

Col. 14, line 17, "ml/Mg/min" should read -- ml/kg/min --.
Col. 16, line 21 (claim 2), "form" should read -- from --.

Signed and Sealed this
Thirtieth Day of December, 1986

Attest:

DONALD J. QUIGG

Attesting Officer

Commissioner of Patents and Trademarks